United States Patent [19]

Moore et al.

[11] Patent Number: 4,773,170

[45] Date of Patent: Sep. 27, 1988

[54] CUSHIONED HEEL INSET FOR POST-OPERATIVE SHOE

[75] Inventors: Robert R. Moore, Hayward; Steve Lamb, Castro Valley, both of Calif.

[73] Assignee: Orthopedic Systems, Inc., Hayward, Calif.

[21] Appl. No.: 50,556

[22] Filed: May 18, 1987

[51] Int. Cl.4 ............................ A43B 3/12; A61F 5/00
[52] U.S. Cl. ...................................... 36/110; 36/11.5; 36/33; 128/83.5
[58] Field of Search ...................... 36/30 A, 110, 11.5, 36/7.5, 33, 86, 37; 128/83.5, 581

[56] References Cited

U.S. PATENT DOCUMENTS

| | | | |
|---|---|---|---|
| 4,188,735 | 2/1980 | Hahn | 36/11.5 |
| 4,314,412 | 2/1982 | Anderson et al. | 36/11.5 X |
| 4,567,678 | 2/1986 | Morgan et al. | 36/11.5 X |
| 4,602,626 | 7/1986 | Johnson | 128/83.5 |
| 4,677,767 | 7/1987 | Darby | 36/110 X |

*Primary Examiner*—James Kee Chi
*Attorney, Agent, or Firm*—Bielen & Peterson

[57] ABSTRACT

A cushioned heel inset for an orthopedic, postoperative shoe. The shoe has a lightweight, rigid orthopedic sole with a skid proof outer sole and a cushioned inner sole, the heel of the rigid sole having a recess for inset of a cushioning pad which interfaces the inner sole.

3 Claims, 1 Drawing Sheet

CUSHIONED HEEL INSET FOR POST-OPERATIVE SHOE

BACKGROUND OF THE INVENTION

The post operative orthopedic shoe of this invention is designed to allow the wearer to be as ambulatory as possible with or without the aide of crutches or the like. It has been discovered that a protective shoe for post operative patients must be both lightweight and rigid. Rigidity is customarily provided by a formed sole that is fabricated of wood. Wood is both lightweight, rigid and able to withstand substantial abuse. The contoured wooden sole is conventionally connected to the wearer's foot, which is often encased in bandages, by a fabric upper which has adjustable straps to wrap and secure the uppers around the wearer's foot.

In order to insure that the wearer does not slip using wooden sole shoes, the wooden sole often has a slip proof outer sole fabricated from an abrasive resistant rubber-like material. Further, in order to provide a minimal comfort to the wearer's foot or some minimal cushioning to the contact interface between the user's heel and the hard sole, a foam covering inner sole is usually provided on top of the wooden core. For most applications, this construction is effective and efficient.

However, as the patient becomes more ambulatory, it has been found that greater protections may be required for the user's comfort. For example, in the cast shoe of Beightol, U.S. Pat. No. 3,566,487, issued Mar. 2, 1971, the rigid sole or platform of the cast shoe is covered with a thick flexible resilient layer running the entire length of the shoe. While the resilient layer provides substantial cushioning, the relatively stable contact between the foot and the rigid sole is lost. Similarly, while the construction of the cast shoe of Debusk, U.S. Pat. No. 3,905,135, issued Sept. 16, 1975, provides a cushioning pad for the heel of the cast, the padding is incorporated at the back of the shoe in the cloth upper and does not noticeably cushion the underfoot of the wearer. In the shoe of Pols, U.S. Pat. No. 4,178,703, issued Dec. 18, 1979, the shoe includes both a flexible upper sole and flexible bottom sole without any rigid core. This construction adequately provides for cushioning in a foot encased in a cast but fails to provide the necessary rigid support for the foot of a patient who is not in a cast and is recovering from minor or major foot surgery.

The cushioned inset of the present invention is designed as a compromise between the desire for a rigid supporting sole and the wearer's comfort, particularly at the location of the heel which encounters the greatest shock during walking. Cast shoes, while similar in appearance and construction to postoperative shoes for foot surgery, can tolerate substantial flexibility in the shoe platform not desirable for postoperative shoes.

SUMMARY OF THE INVENTION

The postoperative shoe of this invention comprises a lightweight open shoe for postoperative patients recovering from foot surgery. The shoe can also be worn for other medical conditions resulting in swelling or tenderness, or whenever the foot requires an open aerated but rigid platform for support. The particular novel feature of the present shoe resides in the construction of the sole. The sole utilizes a conventional three ply construction with a thick contoured inner sole that provides a core for a lamination of a thin foam upper sole and a thin corregated rubber bottom sole. The upper sole provides some cushioning and a resistance to foot slippage on the wooden sole. A rubber-like bottom sole provides a skid proof surface for the otherwise slippery characteristic of unprotected wood. It has been found that hollowing out a preferably oblong recess in the upper portion of the heel of the inner sole or core does not noticeably detract from the structural integrity of the core. The recess can then be filled with a cushioning material to provide an inset under the thin upper sole. Thus, when the often sensitive heel of the patient's foot contacts the heel portion of the platform it will have additional cushioning. This additional cushioning is provided for vertical impact, yet lateral stability is substantially the same. In essence, a substantial degree of heel cushioning is provided and the structural integrity of the shoe which is expected from wooden core shoes of this type, is unimpaired. A physician is confident that he is utilizing an orthopedic shoe that will meet his expectations, yet provide the patient with a moderate degree of additional comfort.

DETAILED DESCRIPTION OF THE PREFERRED EMBODIMENT

Figure 1:
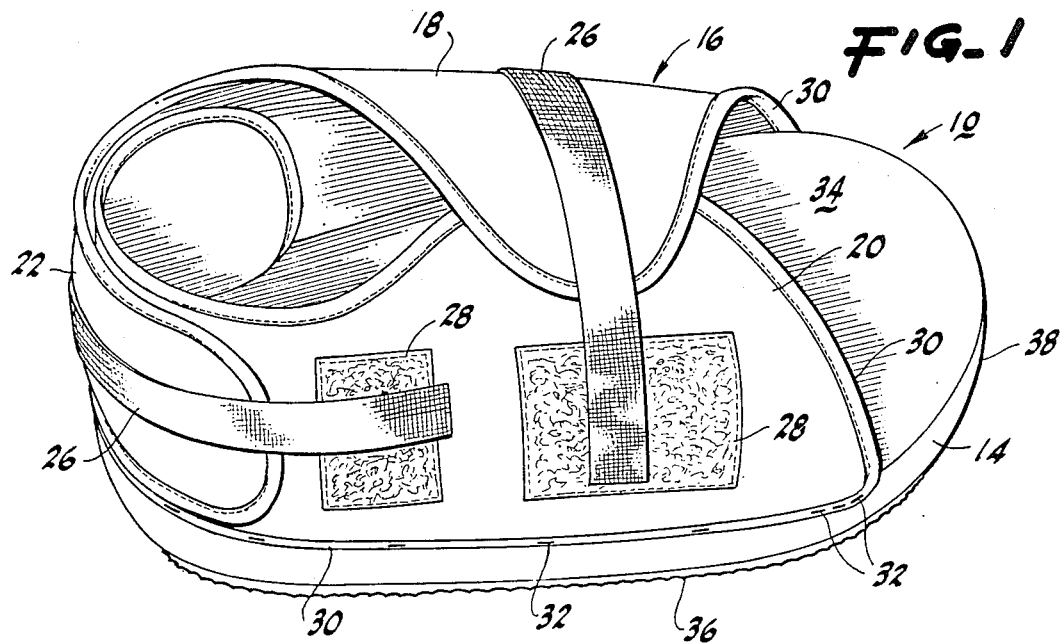
FIG. 1 is a side elevational view of the othopedic shoe.

An orthopedic postoperative shoe, of the type incorporating the improvement of this invention, is shown in FIG. 1 and designated generally by the reference numeral 10. The shoe 10 is constructed with a rigid, preferably wooden sole 14 to which is attached a soft, fabric upper 16. The upper 16 is fabricated with an open toe and two side flaps 18 and 20, one of which has a heel portion 22 which wraps around the heel of the shoe and overlaps the opposed side flap 20. This open construction allows an injured foot, or one on which an operation has been recently performed, to be comfortably seated on the sole before the flaps are wrapped around the injured and often bandaged foot. The soft and flexible upper 16 includes Velcro ® straps 26 which are fastened to one of the upper flaps and engage a complimentary pad 28 on the opposite flap. The fabric uppers 18 include a peripheral bead 30 which provides a trim surface for stapling the uppers to the wooden sole with a plurality of metallic staples 32.

The sole 14 of the cast shoe 10 has an upper cushioning sole 34 fabricated from a closed polymer foam such as polyurethane. The upper sole is of a uniform thickness and is laminated to the flat top surface of the wooden platform sole. The wooden sole 14 has a bottom or lower sole 36 which is constructed from a rubber-like material with an outer corregated surface for resistance of slippage and wear. A bottom sole is also laminated to the under side of the wooden platform sole 14 and conforms to the uplifted toe section 38 of the wooden sole.

Figure 2:
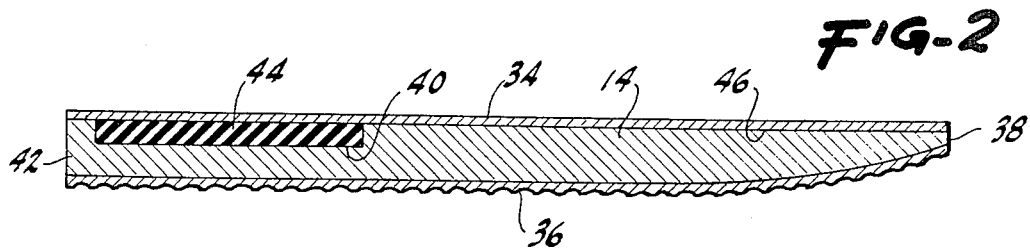
FIG. 2 is a cross sectional view of the sole of the shoe of FIG. 1.
Figure 3:
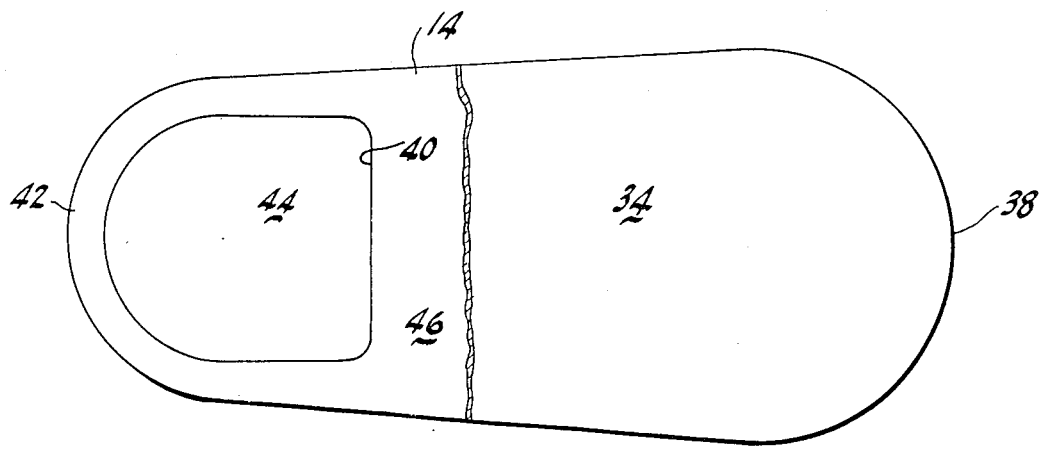
FIG. 3 is a top plan view of a portion of the sole of FIG. 2.

The improved heel construction is concealed from superficial observation and is shown in FIGS. 2 and 3. In the cross-sectional view of FIG. 2, the internal construction of the laminated sole is revealed. As shown, the wooden core 14, which provides the structural integrity for the laminated members of the sole, has a recess 40 milled into heel section 42 of the core 14. While the recess can be of various configurations, one that is oblong and of uniform depth is preferred. Into the recess is installed and glued a rubber or neoprene inset 44 of thickness that conforms to the flat upper surface 46 of the wooden sole. In this manner, the overlying upper sole 34 covers and conceals the rubber inset 44. The rubber inset may be of man-made materials, such a neoprene, and is less compressible than the foam overlay 34 such that moderate additional cushioning is provided to the heel area without the overall structural integrity of the sole 14 being impaired.

While in the foregoing embodiments of the present invention have been set forth in considerable detail for the purposes of making a complete disclosure of the invention, it may be apparent to those of skill in the art that numerous changes may be made in such detail without departing from the spirit and principles of the invention.

What is claimed is:

1. An orthopedic shoe comprising:

a lightweight, rigid platform sole with a toe portion and a heel portion, the platform sole having a substantially flat top and a substantially flat bottom with a thin inner sole uniformly laminated to the top, a uniform outer sole laminated to the bottom and a flexible upper secured peripherally around the platform sole, wherein the platform sole has a substantially uniform thickness tapering at the toe portion, a recess in the top of the heel portion forming a hollow of depth less than the thickness of the rigid platform sole, and an inset of cushioning material in the recess covered by the inner sole such that the structural integrity of the rigid platform sole is unaffected.

2. The orthopedic shoe of claim 1 wherein the inset is fabricated from a rubber-like material.

3. The orthopedic shoe of claim 1 wherein the recess is of uniform depth and has an oblong configuration and the inset conforms to the depth and configuration of the recess.

* * * * *